United States Patent
Boender et al.

(10) Patent No.: US 12,004,973 B2
(45) Date of Patent: Jun. 11, 2024

(54) PROSTHESIS CONNECTION SYSTEM

(71) Applicants: Jay Erna Amandala Boender, Oxford (GB); Jona Aelrid Brendan Boender, Oxford (GB); Jennifer Anne Boender, Oxford (GB); Jacob Quintus Laurens Anthony Boender, Oxford (GB)

(72) Inventors: Jay Erna Amandala Boender, Oxford (GB); Jona Aelrid Brendan Boender, Oxford (GB); Jennifer Anne Boender, Oxford (GB); Jacob Quintus Laurens Anthony Boender, Oxford (GB)

( * ) Notice: Subject to any disclaimer, the term of this patent is extended or adjusted under 35 U.S.C. 154(b) by 33 days.

(21) Appl. No.: 17/878,119

(22) Filed: Aug. 1, 2022

(65) Prior Publication Data
US 2023/0036563 A1    Feb. 2, 2023

(30) Foreign Application Priority Data
Aug. 2, 2021   (GB) ..................... 2111122

(51) Int. Cl.
*A61F 2/78*   (2006.01)
*A61F 2/54*   (2006.01)
*A61F 2/60*   (2006.01)
*A61F 2/50*   (2006.01)

(52) U.S. Cl.
CPC .......... *A61F 2/78* (2013.01); *A61F 2/54* (2013.01); *A61F 2/60* (2013.01); *A61F 2002/5083* (2013.01)

(58) Field of Classification Search
CPC ...... A61F 2/78; A61F 2/54; A61F 2/60; A61F 2002/5083; A61F 2002/30329
See application file for complete search history.

(56) References Cited

U.S. PATENT DOCUMENTS

| 5,013,325 A | 5/1991 | Rennerfelt |
| 5,941,912 A * | 8/1999 | Taylor ................... A61F 2/76 623/28 |

(Continued)

OTHER PUBLICATIONS

Publication of Corresponding GB application No. 2111122.4, UK Publication 2609460, with search report (34 pages).

(Continued)

*Primary Examiner* — Bruce E Snow
(74) *Attorney, Agent, or Firm* — Anderson Gorecki LLP (57) ABSTRACT

A prosthesis includes first and second prosthetic limb components and a fastening system for fastening the first and second prosthetic limb components. The first prosthetic limb component is provided with a first coupling member and the second prosthetic limb component is provided with a second coupling member. The first coupling member includes a cylindric member having an axis, with a wall generally parallel with said axis. The second coupling member includes a circular skirt element having an axis and having corresponding external dimensions to the cylindric member whereby to permit a sliding fit therewith in an unfastened state. The fastening system includes a resilient member having an axis and is operable to expand laterally, orthogonally with respect to the axis such that, in a coupling mode of operation, the lateral expansion operates to cause the skirt to be in a state of frictional engagement with the other coupling member.

13 Claims, 10 Drawing Sheets

(56) References Cited

U.S. PATENT DOCUMENTS

| | | | |
|---|---|---|---|
| 6,123,732 A * | 9/2000 | Gramnas | A61F 2/76 |
| | | | 623/38 |
| 6,231,618 B1 | 5/2001 | Schall et al. | |
| 6,458,163 B1 * | 10/2002 | Slemker | A61F 2/76 |
| | | | 623/38 |
| 7,488,349 B2 | 2/2009 | Einarsson | |
| 10,398,577 B2 | 9/2019 | Dillingham | |
| 10,772,745 B2 * | 9/2020 | Porter | A61F 2/78 |
| 2012/0310371 A1 | 12/2012 | Bachus et al. | |
| 2014/0135943 A1 * | 5/2014 | Klotz | A61F 2/4014 |
| | | | 623/23.46 |
| 2020/0368041 A1 | 11/2020 | Beerens et al. | |

OTHER PUBLICATIONS

Publication of Corresponding application 2032651 in the Netherlands (33 pages).
Search Report from NL 2032651 (9 pages).
GB Search Report dated Jun. 23, 2022 from corresponding GB application No. 2111122.4 (2 pages).
GB Search Report dated Jun. 23, 2022 from corresponding GB application No. 2111122.4 (1 page).

* cited by examiner

PROSTHESIS CONNECTION SYSTEM

FIELD OF THE INVENTION

The invention relates to the field of prosthetics limbs in general and, in particular to the field of connection a prosthetic limb to a limb reception member. The present invention relates more particularly to a socket system for a prosthesis, to enable attachment to a reception part associated with a stump associated with a wearer of the prosthesis.

BACKGROUND OF THE INVENTION

Figure 1A:
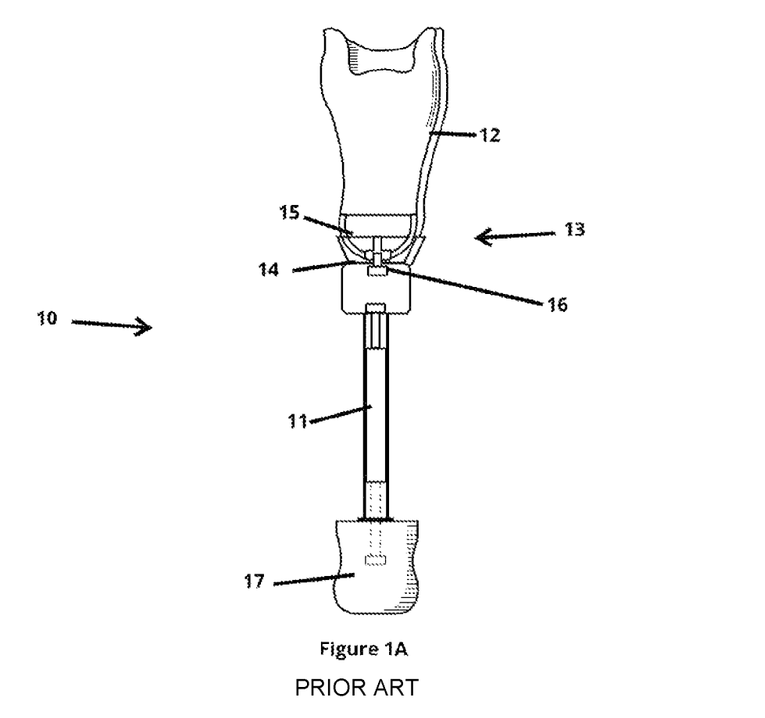
FIG. 1A shows a known simple limb receiving element to foot prosthesis.

Prosthesis socket systems for limbs typically comprise a prosthetic limb and a limb reception member. Such systems have been known for years; over time a development was such that a separable socket system was introduced. As shown in FIG. 1A, there is shown a prosthesis socket system 10 for lower limbs typically comprising a prosthetic limb 11—specifically a prosthetic femur, a limb reception member 12 and a separable socket attachment system 13. The example shown dates from the 1960s and does not provide any flexion about the socket—which would otherwise comprise a knee joint; rather this teaching provides an arrangement of fixings being a spherical, cup-like load bearing member 14, a corresponding spherical member 15 associated with the limb reception member 12 seat and a threaded fastener 16. The threaded fastener provided an element of adjustment such that a prosthetic foot 17 could be utilized, with an appropriate direction of the foot relative to the amputee's stump received by the reception member 12. This development provided a dynamic prosthetic alignment means which enabled periodic realignment to compensate for changes in a patient. Moreover, such apparatus was inexpensive and easily constructed, whilst capable of being manufactured such that it was of light weight and adequate strength. In recent times, such joint-less, so-called peg-leg, systems have generally been replaced with prosthetic legs with an operable knee joint.

The prosthesis socket also has a distal end, on which distal prosthetic elements can be arranged via an adapter element. These prosthetic elements are generally simulations of amputated limbs, for example of a foot, a lower leg or a hand. Particularly in the case of prosthetic legs, enormous forces sometimes have to be taken up both by the distal prosthetic elements and also by the prosthesis socket, for example during walking with the prosthesis. For this reason, it is necessary that, on the one hand, the prosthesis socket itself is stable and robust and that, on the other hand, a firm and secure connection of the prosthesis socket to the distal prosthetic element is ensured.

Figure 1B:
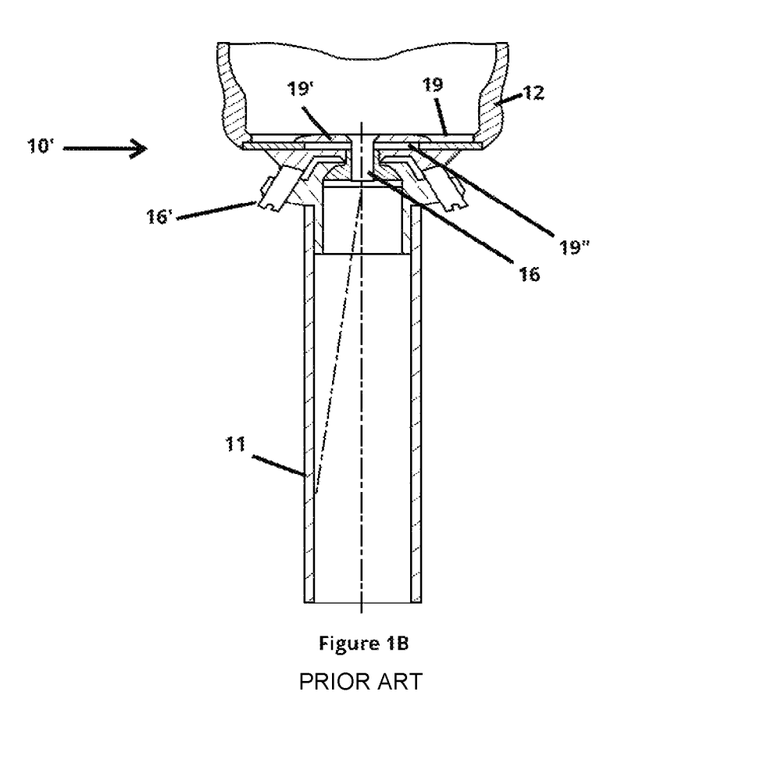
FIG. 1B shows a known simple alternative fastening between a limb receiving element and prosthetic leg.

Unfortunately, many modern connector assemblies are either very complex or provide a limited range of permissible adjustment. For example, U.S. Pat. No. 5,013,325 per FIG. 1B discloses a socket 10' for a prosthetic arrangement comprising an end plate 19 and a cylindrical wall 12 extending upwardly therefrom. A circular opening 19" is disposed in the end plate, and a circular washer 19' is disposed over the opening and against the end plate 19. A bolt 16 extends through the washer 19' and through the opening for attachment to a prosthetic limb 11. As the position of the limb is adjusted, conveniently by means of radially disposed adjustment bolts 16', the bolt and circular disc will move relative to the circular opening. To achieve the maximum possible adjustment, the circular opening should be as large as possible to permit the bolt to have the widest range of movement. As the opening is expanded, however, the disc must also be expanded to remain larger than the opening. Unfortunately, the movement of the disc is restricted by the cylindrical wall of the socket and a large disc will have a small range of movement within the socket. Therefore, due to the competing constraints of disc size and opening size, maximum available adjustment is limited. Moreover, no knee pivot axis is provided. It will be appreciated that these adjustment bolts and other coupling arrangements hinder any aesthetic elegance. Whilst an amputee will at times not want to display their disability, it is becoming increasingly common for amputees not to be embarrassed by their prosthetic limb; a limb that looks "cool" is one that will be worn with pride.

Figure 2A:
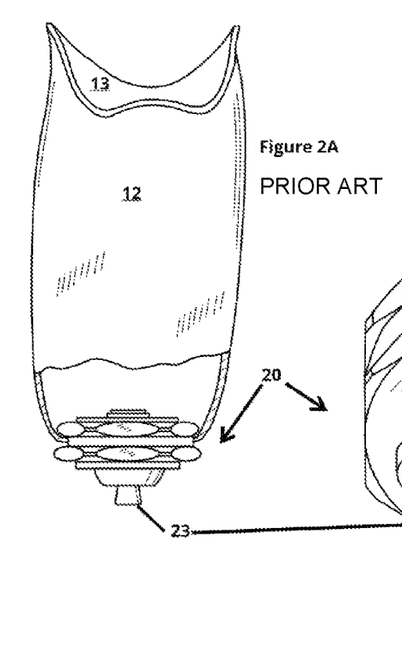
FIGS. 2A and 2B show a known second simple limb receiving element with a distal stump connector in detail.
Figure 2B:
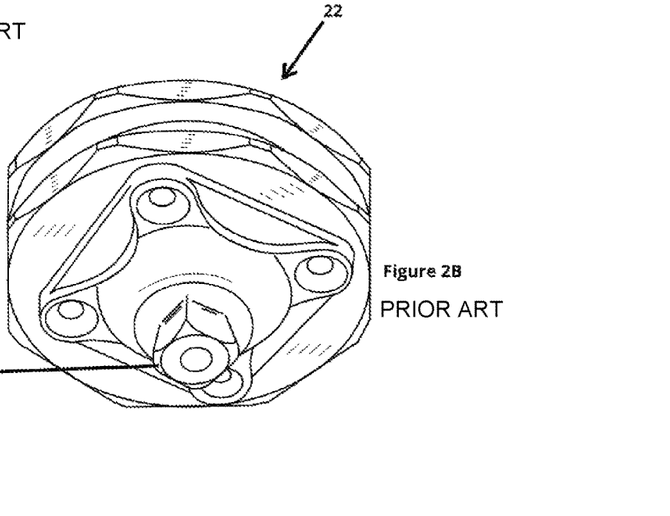

With reference to FIG. 2A, an example of an easily separable system is shown: a limb reception member 12 is provided with a separable socket system assembly 20 with generally circular coupling members including screw fastening flanges 22 having an inverted pyramid element 23, detailed in FIG. 2B, which provides angular locking, rotational as well as axial locking. At the upper end of the prosthesis socket 12 in FIG. 2A, a proximal opening 13 is shown into which an amputation stump, in this case a below-knee stump, can be inserted.

Figure 3A:
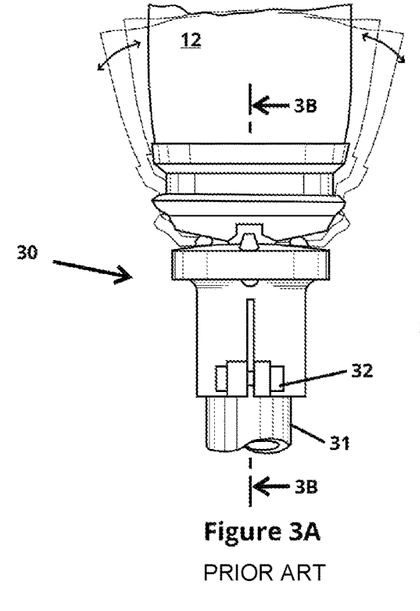
FIGS. 3A, 3B and 3C show a known third simple limb receiving element with a distal stump connector in cross-section and a plan view of the inside of the limb receiving element.
Figure 3B:
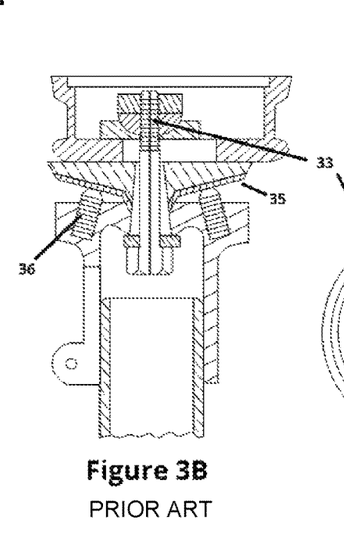
Figure 3C:
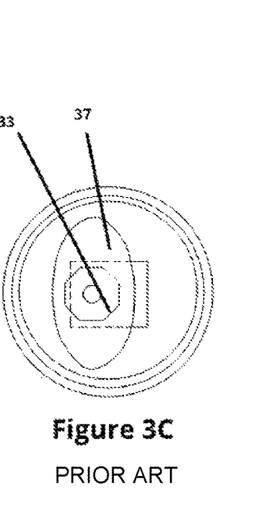

FIG. 3A shows a further assembly 30 of attaching the shaft of a prosthetic limb member 31, which limb member 31 is fastened by means of a screw-threaded fastener 32. The assembly 30 is fastened to limb reception member 12 by means of bolt fastening means 33, detailed in FIG. 3B, being a cross-section as indicated in FIG. 3A, which permits planar movement across the plane of the end plate 34 distal end of the limb member, whilst a curved cup member 35 with adjustment bolts 36 enable angular fore and aft adjustment movements to be accommodated. FIG. 3C shows how an inside aspect of the limb reception member 12—without any necessary padding present—with a washer 37 supporting bolt means 33, which is fastened upon set-up to prevent any planar motion in use.

Figure 4A:
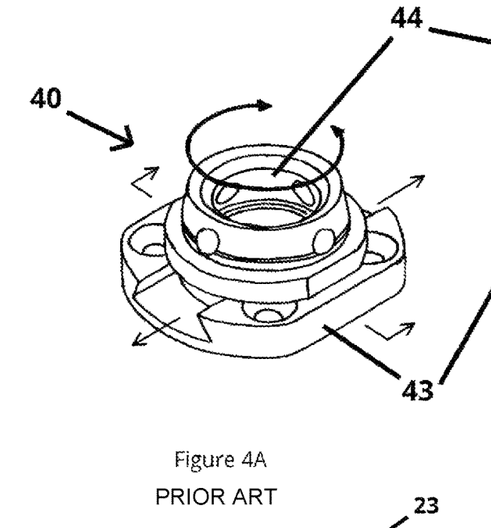
FIGS. 4A and 4B show two known slidable socket systems used as a connector between a limb receiving element and a prosthesis.
Figure 4B:
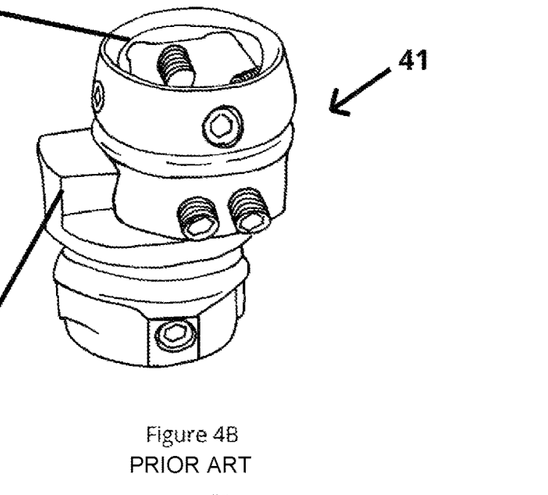
Figures 4C, 4D:
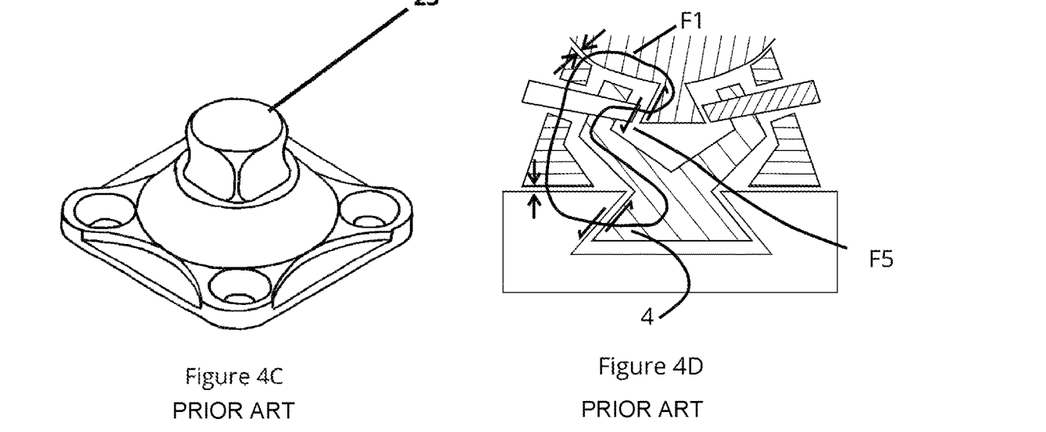
FIG. 4D shows the forces arising in attachment in a connector per FIG. 4B.
FIG. 4C shows a known second inverted pyramid connector.

FIGS. 4A and 4B show two further types of assemblies 40, 41 wherein a first connection member 42 slidably moves for adjustment and setting up with respect to a second connection member 43, prior to clamping of respective components. FIG. 4A shows a dove tail construction that by means of friction prevents slippage, and prevents rotation from occurring. Each first connection member 43 has an aperture 44 to connect with an inverted pyramid connector being a variation of the inverted pyramid connector as shown in FIG. 2B. FIG. 4B shows a type of assembly 41 that generates friction without necessary interlocking. The dovetail construction provides interlocking in all degrees of freedom but the direction of intended and permitted slide. The set screws provide a restraining friction force, which said friction prevents the slide movement to take place. FIG. 4C shows an inverted pyramid 23 that interlocks with a suitable receiver (not shown). FIG. 4D indicates forces associated with a known connection member 4. FIG. 4D shows a force loop F1, where the force loop creates friction in mutually abutting surfaces by compression forces once tightened. The fastener forces F5 are symmetrical and substantially opposing, reducing the net generated compression force in contact face sets.

Figure 5:
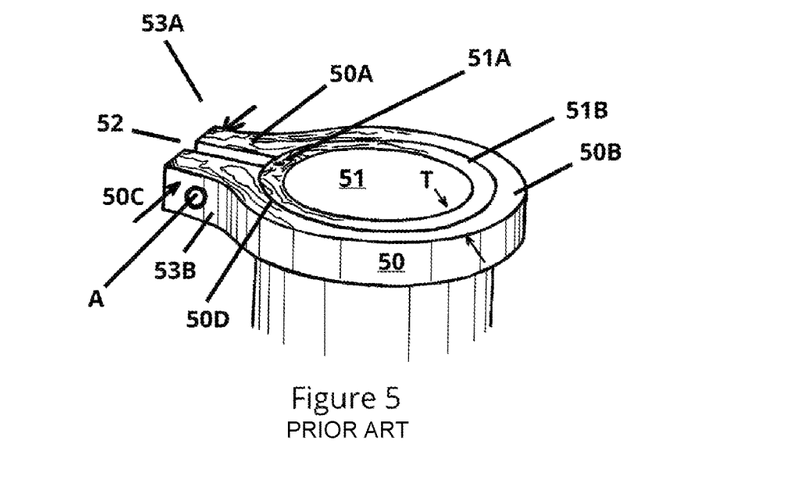
FIG. 5 show a known compression ring fastener.

FIG. 5 shows a prior art example of an external clamp 50 about a generally circular structure, in this case a tube 51. The fastener comprises a generally circular body, with a slot 52 defined between two clamping flange parts 53A, 53B which are urged together by means of a screwthreaded bolt, whereby to provide a circumferential tightening about the end of the tube 51, so as to provide a friction clamp, operable to resist axial and rotational relative displacement between clamp 50 and tube 51. This simple arrangement has some disadvantages in that the same friction causes a poorly distributed clamping force on flange parts 53A, 53B. This Figure indicates a finite element analysis of stresses in the assembly parts: clamp 50 clamping on internal structure 51, by pinch force G causes stress fields 50A and 51A, respectively in the clamp and in the internal structure 51. The friction between the clamp and the internal structure causes an uneven distribution of stress field fringes 50A and 50B, and the stress fields are absent on opposite side at locations 50B and 51B. The disparity of friction clamp force not only excessively stresses the components on one side leading to a risk of failure by fracture, but additionally, the inconsistent levels of friction forces between the clamp component and the clamped component are cause of noise as the parts slip and move where friction forces are too low to avoid movement. The ability of axial length adjustability and adjustability of rotation position is a strength of the design at a cost of high stress and inefficient use of fastener generated force leading to the mentioned drawbacks of slip and noise.

It is clear in that by providing a connection between two components by means of friction generated by a single pinch bolt about the circular structure 51, whilst providing an effective interference fit, is ineffective in securing uniform material stresses about the components thereby fastened and ineffective in creating a well distributed friction (and high local contact stress in the material surfaces). The unequal distribution of contact friction will inevitably permit relative slippage of certain faces of the contacting surfaces to slip past one another, whilst certain other faces of the contacting surfaces cannot slip. The relative movement gives rise to noises which at best are annoying, giving rise to a loss of confidence in use in the prosthetic limb as the amputee applies complex loading and unloading forces on the assemblies.

A further drawback of this type of structure is the need to increase the wall thickness T of the internal tubular structure 51 (in FIG. 5) to deal with the stress fields 51A. This leads to additional prosthesis weight that is disadvantageous to the amputee.

In summary, known systems have addressed connections between component limb parts in accordance with three main principles: i) connections with fasteners that have a head larger than an aperture hole it 'penetrates' to secure the component onto another component, for example as exemplified by FIG. 1A, where a fastener 16 is secured with respect to an aperture to 14. This system locks in all degrees of freedom by interfering shape restraint, noting that axial rotation and axial length tuning are excluded from these designs, unless additional shimming parts are used. ii) The dovetail construction, as shown in FIGS. 4A, and 4B provides interlocking in all degrees of freedom but the direction of intended and permitted slide. The set screws provide a restraining friction force, which said friction prevents the slide movement to take place. The loss of effective fastening forces due to improper and inefficient force angles is surprisingly prevalent. Rotation is controlled by friction, adjustment to axial length of these assemblies for fine tuning of the prosthesis requires additional components.

As discussed above there are several types of connections provided between limb reception members and prosthetic limbs. It is to be noted that only simple limbs have been shown in FIGS. 1-4; in the event that an articulated prosthetic limb member is employed, with, for example, hydraulic extension and damping features, it will be realized that a safe and comfortable prosthesis demands a secure connection, noting that it is quite often that first and second lower limbs are prosthetics. Diabetic amputees may also typically suffer from being overweight, whereby any misdirection/ loose fitting or otherwise can so easily result in a fall. A direct consequence of the above is that a patient will either get used to a particular prosthetic limb element or may have their condition aggravated by a particular component. In the field of modular prosthetics there are a range of connectors, of which the more common connectors are referred to as: which are generally referred to as: Tube adapters; Pyramid adapters; European four hole adapters; M36 screw thread adapters, whilst there are also systems appropriate for children and there are niche adapters, where, for example, through knee amputations has been necessary. It is not economical to furnish complex prosthetic components such as knee joints with such a gamut of interfaces to mate with proximal and distal connecting parts.

SUMMARY OF THE INVENTION

The present invention seeks to provide an improved inter-component prosthetic connection arrangement. The present invention seeks to provide to a universal interface to a complex prosthetic component (such as prosthetic joints or feet) and to provide an improved distribution of forces that arise within a modular prosthetic connection system, in use. An additional object of the invention is also to propose a socket system for a prosthesis, by means of which the person wearing the prosthesis has greater confidence in the prosthesis and, at the same time, distal prosthetic elements can be attached in a secure and stable manner to the socket system.

In accordance with a first aspect of the invention, there is provided a prosthesis including a first prosthetic limb component, a second prosthetic limb component, and a fastening system, for fastening the first prosthetic limb component to the second prosthetic limb component; wherein the first prosthetic limb component is provided with a first coupling member and the second prosthetic limb component is provided with a second coupling member; wherein the first coupling member comprising a cylindric member having an axis, with a wall generally parallel with said axis; Wherein the second coupling member comprises a circular skirt element having an axis and having corresponding external dimensions to the cylindric member whereby to permit a sliding fit therewith in an unfastened state; wherein the fastening system, associated with one of the first or second coupling members comprises a resilient member having an axis and wherein the resilient member is operable to expand laterally, orthogonally with respect to the axis, said axis being coaxial with the axis of the coupling member with which it is attached; wherein the fastening system is arranged such that, in a coupling mode of operation, the lateral expansion operates to cause the skirt to be in a state of frictional engagement with the other coupling member; whereby the first and second coupling members couple together with associated first and second prosthetic limb components. By the provision of such a prosthesis system, a number of benefits of the invention become apparent; the transfer of forces within a connector are balanced, whereby to reduce chance of failure or discomfort in use together with an elimination of untoward sounds arising from unbalanced forces of retention of the connection of components. By reducing unwanted stress in construction, the components need not be so substantial, assisting in achievement of a reduction in overall mass, given that to compensate in substantial forces, reinforcement members, adding mass are required. This provides a direct benefit in a reduced cost of material, size of product, which is of benefit to those who might be, to a degree, embarrassed or inconvenienced by the wearing of a prosthetic device. It will be appreciated that where less mass is involved, the overall aesthetic appearance can be improved.

The prosthetic system is applicable to numerous applications and can be arranged such that the first prosthetic limb component is a prosthetic limb and comprises one of a shin member, lower arm, foot or a hand, and the second prosthetic limb component is operable to receive a stump of a patient. Equally the roles of the respective first and second prosthetic limb components are reversed, as may be required for a particular set of circumstances.

In accordance with another aspect of the inventions, there is provided a coupling unit for use in a prosthesis. The coupling unit may be a separate component, and may be associated with a prosthesis or a prosthesis coupling unit. The coupling unit enables a prosthesis of known design to be coupled with a limb receiving component in accordance with the present invention and permits inter-operability of components of different brands. Indeed, the prosthetic system can be arranged such that the first prosthetic limb component is a prosthetic limb and comprises one of a shin member, lower arm, foot or a hand, and the second prosthetic limb component comprises a coupling member having an additional coupling component and is operable to couple with a known coupling element associated with a prosthetic limb component is operable to receive a stump of a patient. Equally the roles of the respective first and second prosthetic limb components are reversed, as may be required for a particular set of circumstances.

The prosthetic system can be arranged such that the cylindric member is a recess and upon placement of the skirt about the laterally expanding fixing means, the exterior of the skirt frictionally engages with inside walls of the recess.

The prosthetic system can be arranged such that the inside wall surfaces of the skirt are tapered, in a fashion whereby to assist in transfer of forces from the outer edge of the resilient material towards the inside face of the skirt. The cylindric and skirt members may comprise corresponding regular polygons in plan. The cylindric and skirt members may comprise corresponding irregular curvilinear polygons in plan.

The laterally or radially expanding fixing means can be selected from one of the following a star nut; an elastomeric material which can be compressed in a direction perpendicular to an axis of the cylindric member; and a stressed member controlled by a cam-operated member or a screw-threaded member.

The present invention can thus provide a clamping mechanism that distributes forces of connection such that a reduction in the size of components can be realized without loss of overall functional strength, assisting in an overall size. Moreover, by producing a system that enables adaptation between different types of prosthesis enable versatility in use, with an ability to become future proofed by providing an interconnection system operable both with known systems and yet to be conceived connection systems (onward connectivity).

BRIEF DESCRIPTION OF THE DRAWINGS

An illustrative embodiment of the present invention is explained in more detail below with reference to a drawing, in which:

FIGS. 10-12 show further variations of a connector where the proximal interface is an industry standard screw thread/tubular interface, as detailed in FIG. 11A;

DETAILED DESCRIPTION

There will now be described, by way of example only, the best mode contemplated by the inventor for carrying out the present invention. In the following description, numerous specific details are set out in order to provide a complete understanding to the present invention. It will be apparent to those skilled in the art, that the present invention may be put into practice with variations of the specific.

Figure 6A:
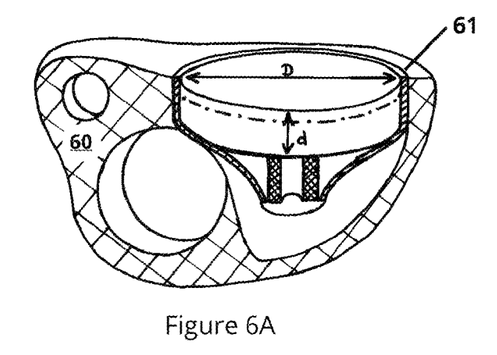
FIG. 6A show a first embodiment of a lower leg prosthesis in accordance in the invention.

FIG. 6A shows an example of a prosthetic socket system 60 according to a first illustrative embodiment of the present invention. The prosthesis socket system is defined at a proximal portion of a tibial prosthesis, with a hydraulic control element not present, to permit a clear view of a cylindrical recess 61 of depth d and a diameter D. The axis of the recess corresponds with an axis of insertion associated with a connection system, with respect to the other prosthetic part to which the system is connected. As will be appreciated, socket systems of this general type are known from the prior art. The prosthesis socket, into the proximal end of which an amputation stump of the patient is inserted when the patient is putting on a prosthesis equipped with such a socket system is not shown. In order to ensure an optimal hold and fit, and in order to cushion the sometimes sensitive amputation stump, a liner made of an elastic material, for example silicone, can first of all be pulled over the amputation stump. The amputation stump thus provided with the liner is then inserted into the prosthesis socket. An index line 62 may be formed, such that it is one of either raised or indented with respect to the recess surface, with corresponding opposite features associated with the outside surface of the skirt whereby the skirt—and the socket—will not be capable of rotating whilst in position, with the compression fitting in operation.

Figure 6B:
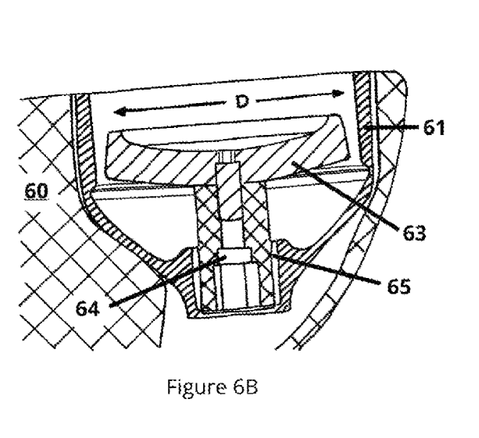
FIG. 6B shows a lower leg prosthesis per FIG. 6 in cross-section, ready to accept a coupling member.
Figure 6C:
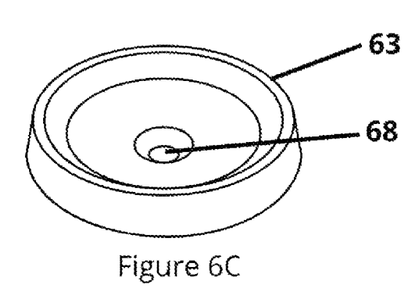
FIGS. 6C & 6D show two forms of cupped discs for resilient retention.
Figure 6D:
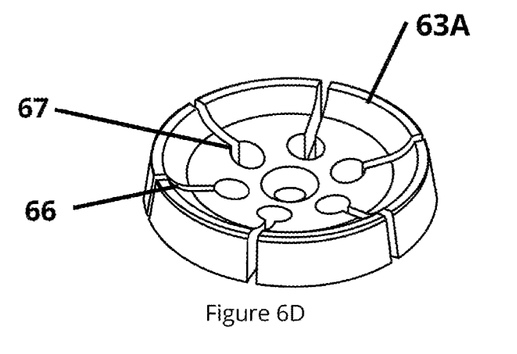
Figure 11A:
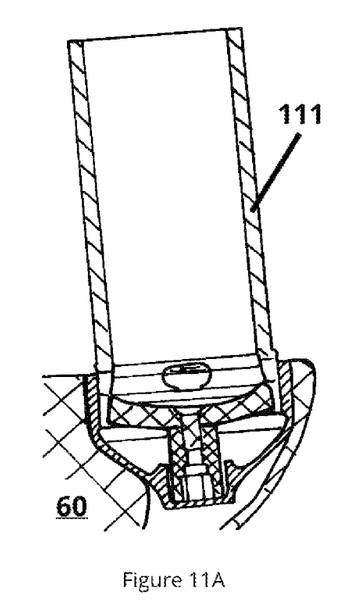

FIG. 6B shows a section through the prosthesis of FIG. 6A, prior to insertion of a connector element such as shown in FIG. 11A, below, that can mate with a corresponding connector of a proximal stump receiving element. The recess member 61 provides a generally circular recess, with upstanding walls, which depend and come together to include a sub-housing 65 operable to retain a screw-threaded bolt 64 which acts to push circumferential expansion member 63: Circumferentially expandable member 63 lies within cylindrical recess/receiving socket 61, which in an unexpanded state defines a circular channel for reception of a skirt element 62 associated with a connector (See FIG. 7). In such an unexpanded state, the skirt element 62 is of a general sliding/interference fit with respect to the inside of the recess 61. The compression fastener element 63, is urged to expand upon the driving of screw-threaded fastener 65, so that the cupped element is caused to have of a reduced axial length. FIG. 6C show a first cupped element 63, which can be made from aluminium for low weight or from thin walled titanium. FIG. 6D provides a first alternative; there is provided a number of slots 66 radially extending from part-circular apertures 67, set a distance from a central aperture 68, which is used to engage with a screwthreaded device 64 or similar; said slots produce anisotropic radial stiffness and circumferential compliance upon fastening.

Figure 6E:
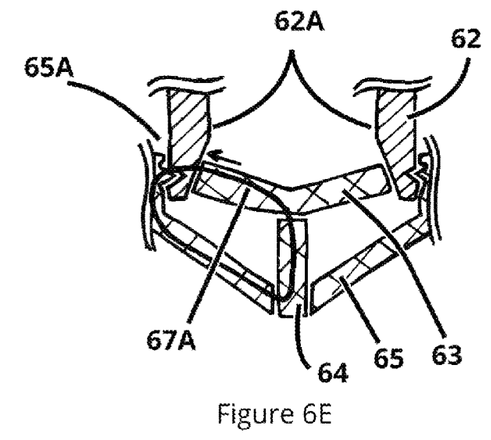
FIGS. 6E & 6F show two further embodiments of the invention in section.
Figure 6F:
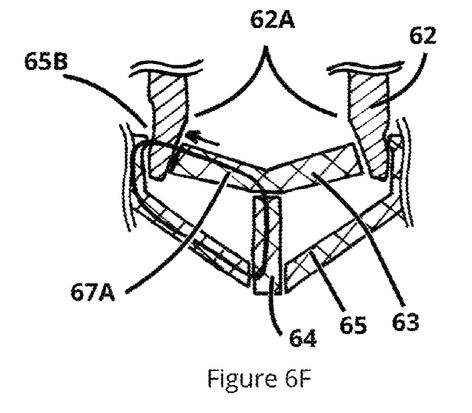

With reference to this figure and FIG. 13A, below, it can be seen that the screw-threaded bolt 64 is arranged to push the centre of the disc (compression fastener element) 63 away from the prosthesis and therefore abuts against the frame 65 of the connector housing. It will be appreciated that the circumferentially/radially expanding element can be caused to expand in a number of different ways, especially as indicated in FIGS. 8C-8E. The outside edge of the fastener element 63 radially expands, in turn causing the skirt 62 to be pushed outwardly, in turn fixing the skirt 62 axially relative to the recess 61. With reference to FIG. 6, an index line (not shown) may be formed, such that it is one of either raised or indented with respect to the recess surface, with corresponding opposite features associated with the outside surface of the skirt whereby the skirt—and the socket—will not be capable of rotating whilst in position, with the compression fitting in operation. In another embodiment, as shown in FIG. 6E, where the clamped aspect of connector 62A is castellated such that the connector 62 terminates with multiple prongs to allow radial securement and high axial rigidity, such to allow an undercut fitment with the base part of the connector 65. This benefits the system in that a resilient bias can be provided to provide a click press fit allows connector 62 to resiliently clip in the undercut 65A in base part of the connector 65. Tightening jack fastener 64, acting on laterally expanding member 63 secures the prongs of connector 62A to be lodged securely in undercut face 65A set). The axial weight of the patient is carried by the preload of the Jack fastener (2), and rotation is prevented by the friction. Continuous force lines are indicated 67A. In yet another embodiment, per FIG. 6F, the undercut is a grooved face 65B whereby the body weight is supported by the exterior face of component 62, whereby inherently preventing a helical freedom of movement.

Figure 7A:
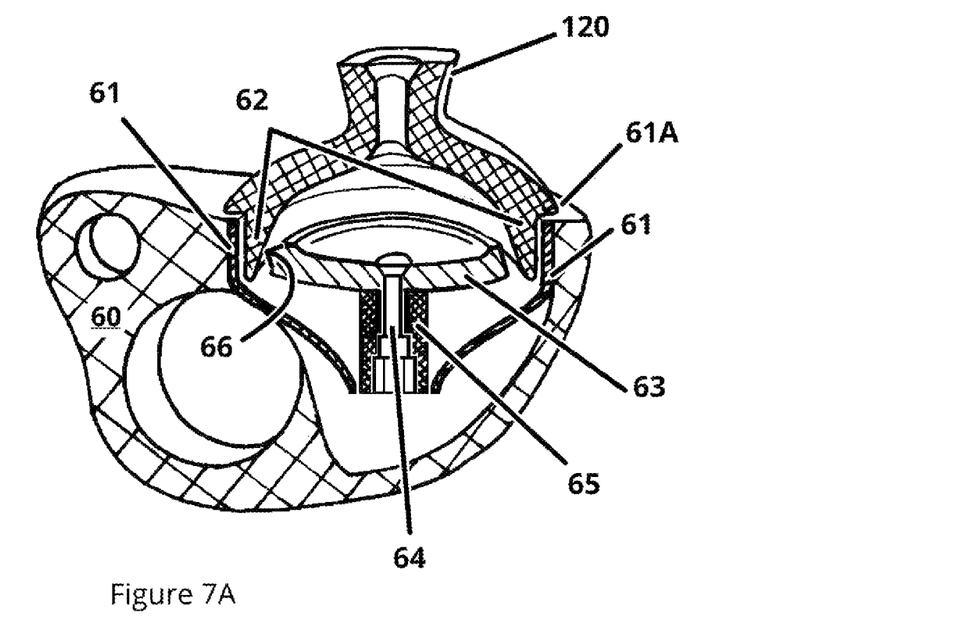
FIGS. 7A and 7B show a prosthesis with an inverted pyramid connector in place, in perspective and cross-section respectively.
Figure 7B:
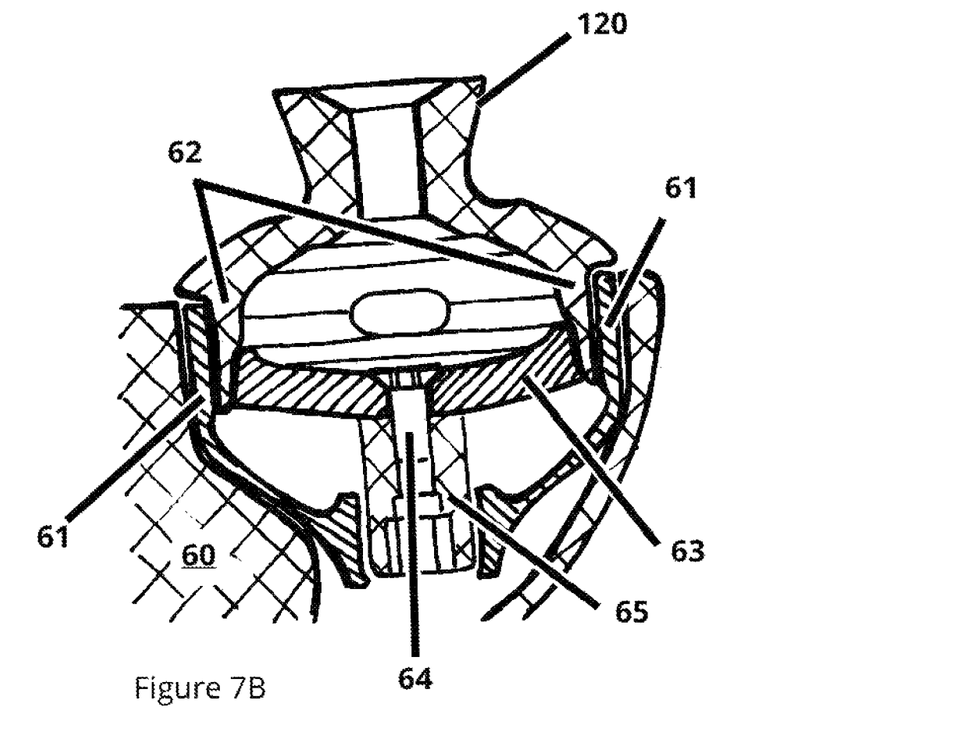

FIG. 7A shows the prosthetic socket system of FIG. 6A with an inverted pyramidal connector 120 in place, the pyramid element being received by a flange plane 61A, with a depending circular skirt, indicated by 62 which has a diameter in correspondence with diameter D, the skirt being of a sliding/interference fit with respect to the inside of the recess 61. A compression fastener element 63, is urged to expand upon the driving of screw-threaded fastener 65 with respect to a part 65 fixed relative to the prosthesis. The outside edge of the fastener element 63 radially expands, in turn causing the skirt 62 to be pushed outwardly, in turn fixing the skirt 62 axially relative to the recess 61. FIG. 7B shows the view of the inverted pyramid connector 120 in cross-section.

An expandable bushing assembly is conveniently associated with a screw-threaded shank of an ordinary bolt creates an expandable diameter bolt that installs freely and easily in a hole. When the nut is tightened against the bushing assembly it becomes radially tight in the hole. Such expandable diameter bolts are as easy to remove as an ordinary nut and bolt and every bit as reusable. Expandable diameter bolts provide the capability of fabricating demountable rigid (minimum deflection under load) structural joints. The extremely tight radial fit of these fasteners makes them ideal for resisting shock loads, severe vibration, reversing, and cyclic shear fatigue type loading.

Figure 8A:
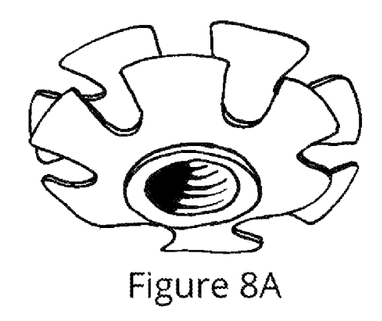
FIGS. 8A-8E show a number of non-limiting examples of radial expanders that are suitable for the present invention.
Figure 8B:
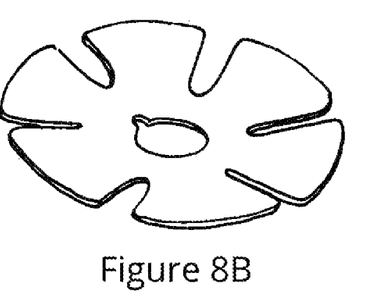
Figure 8C:
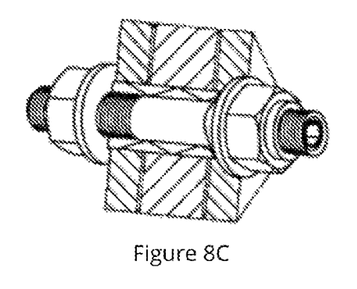
Figure 8D:
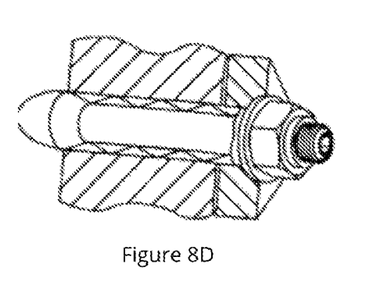
Figure 8E:
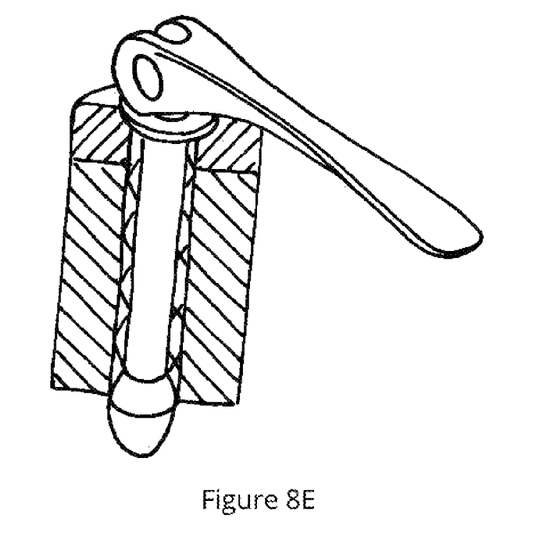

With reference to FIGS. 8A through to 8E, there are shown a number of simple expansion members. FIGS. 8A and 8B comprise, respectively double and single star nuts, or tube connectors, known for example, from bicycle headsets; the edges grip an inside of the tube and as a bolt is tightened, the star shape seeks to adopt a generally flatter profile, with the result that the grip of the star nut against the inside edge of the recess is increased. FIGS. 8C and 8D show, respectively expansion bolts having access at each end and a blind access expansion bolt, both types compressing a resilient element outwardly upon fastening of the respective fastener. FIG. 8E shows a cam-operated radial expansion bolt: —the blind bolt is modified to utilize a cam type handle to expand the bushings rather than a threaded nut, you have a quick-acting expandable diameter pin. Such a pin can be tightened or relaxed by one simple, quick, easy motion, yet when installed, provides a tight radial fit in the hole. When relaxed, there is ample clearance for installation and removal. This type fastener offers high shear capability and, being radially tight in the hole, is applicable in areas of high shear fatigue, high shock loading, and difficult vibration.

Figure 9A:
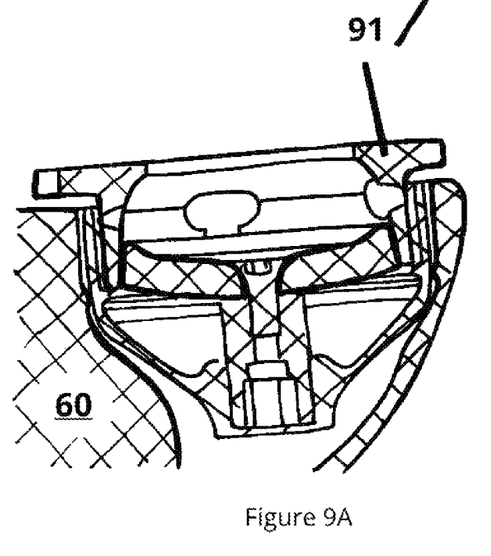
FIGS. 9A and 9B show an alternative embodiment.
Figure 9B:
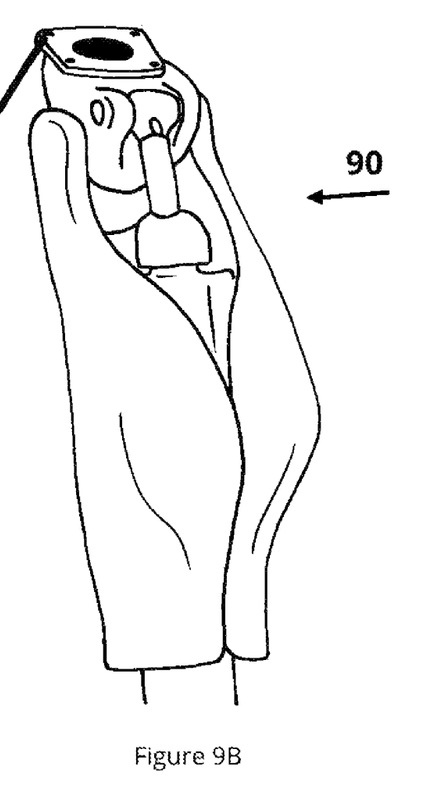
Figure 10:
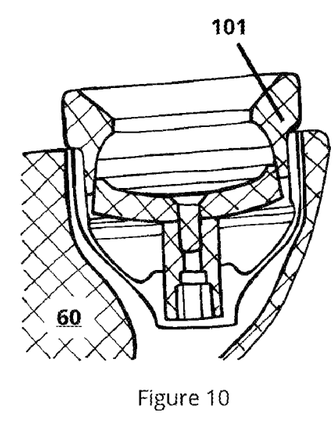
Figure 11B:
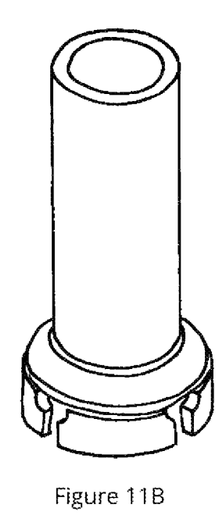

FIG. 9A shows another embodiment, wherein the prosthesis 90 is equipped with a connector 91 adapted to cooperate with a four hole connector system of the corresponding to-be-directly-mated-with another prosthetic part, in this case a limb receiving element, not shown. However, FIG. 9B shows a lower leg prosthesis 90. Coupling connector 91 is provided with four bolt-holes to permit four fastening bolts to said other prosthetic part. FIGS. 10 and 11A show an example upper part of a lower leg prosthesis 60 with a tapered receiving connector 101 and a tube extension connector 111. Referring to FIG. 11B, the proximal interface, or the 'balance of the adapter' is indicated and is machined to represent any proximal interface that has the MTI machine taper interface in association with the disclosure, with reference numeral 60 indicating the distal balance of the limb system.

Figure 12:
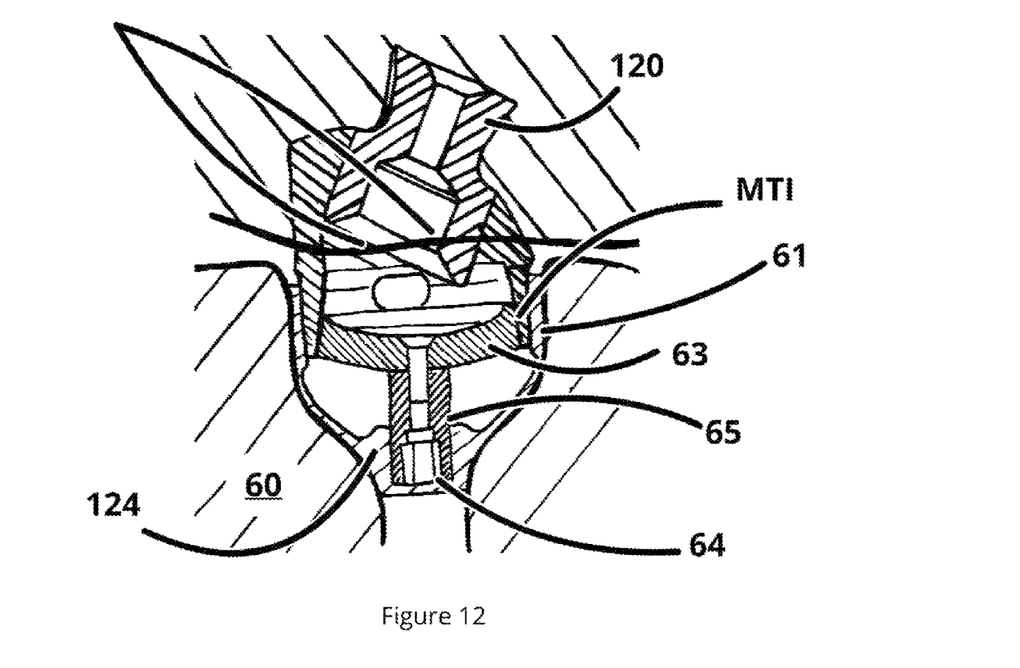

FIG. 12 shows a still further embodiment wherein there is a provided a prosthesis 60 having a socket, with a first axis and an inverted pyramid coupling element 120, associated with the skirt element of the coupler, save that an axis associated with the inverted pyramid is inclined with respect to the first axis, as indicated by the balance of the adapter (BoA). The machined taper interface (MTI) and interlocking interface 61 are also shown in this figure. In this example jacking element 122, driven via a recessed head 64, such as an Allen fastener head is screwthreadedly mounted with respect to the connector 65, which is located within element 124, which depends from socket/recess element 61.

Figure 13A:
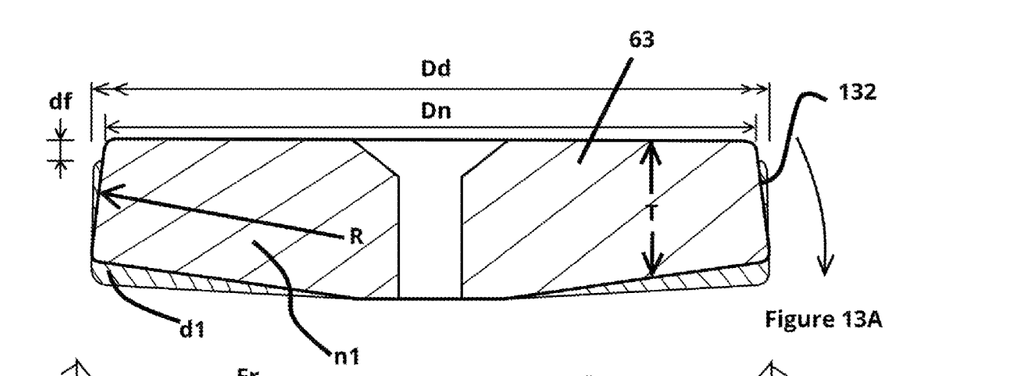
FIGS. 13A, 13B, 14A, 14B, 15A, and 15B show how the forces of attachment associated with an circumferentially expanding element are distributed; and, FIGS. 16A-17B show how forces are applied in relation to prior clamping arrangements.
Figure 13B:
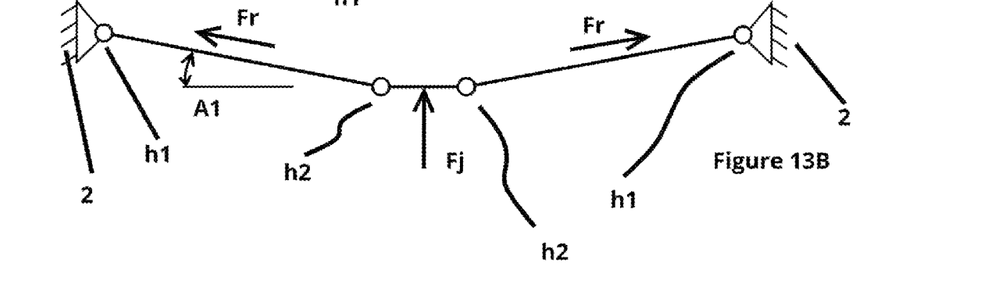

Turning now to FIG. 13A, there is shown in cross-section (through the middle of the circular member) radially expanding member 63 or wedge suitable for fitment in the prosthesis of FIG. 6 in a relaxed state n1 with relaxed diameter Dn; FIG. 13B is a corresponding force diagram with the compression force or jacking force Fj, with a net resultant radial forces Fr. Given that the compression force is zero, per Fr+Fj/sin A1°, the radial forces are also zero. It is to be noted that angle A1 is the simplified representative angle of the wedge where the wedge has an advantageous radius R, to facilitate a rolling action on the machine taper face of restraining prosthetic adapter in turn also restrained in the housing 61, per FIG. 15A and as indicated by reference numeral 2 in FIG. 13B. FIG. 13A also represents the radially expanding member 63 in a loaded state d1 with a correspondingly deformed shape with an increased diameter Dd. Per FIG. 13B, the axial compression force or jacking force, per Fr+Fj/sin A1°, the radial forces define a functional load.

FIG. 13A represents the rolling action on the restraining outer contour of the wedge as a pivot h1, and the flexural aspect of the centre of the wedge as a hinge (h2). The goniometry predicts the maximum force amplification Fr=Fj/sin(A1), where Fr>>Fj. In the event that angle A1<30°, then 1/sin A1>2–i.e. realizing an amplification factor of more than 2. Advantageously, angle A1 as chosen to be nearer to 10°, meaning 1/sin A1=5.7, a maximum amplification factor of 5.7. Naturally the representation of the pivot points h1, h2 are not ideal, and the angle A1 will not be precisely known; moreover, the flexural properties of the resilient member will affect the pivot properties. Nonetheless, it will be understood that Fr>Fj, and therefore the jacking force Fj will be amplified by a factor greater than one. It has been found helpful for the inside surface of skirt to be tapered, such that the outside edge surface of a cupped resilient element having thickness T, will permit the direction of the force vector Fr to approach the axis of a normal vector arising from the tapered contact surface. It will be appreciated that the taper angle will be within a range of 1-15° with respect to the axis of the skirt element.

Figures 14A, 14B:
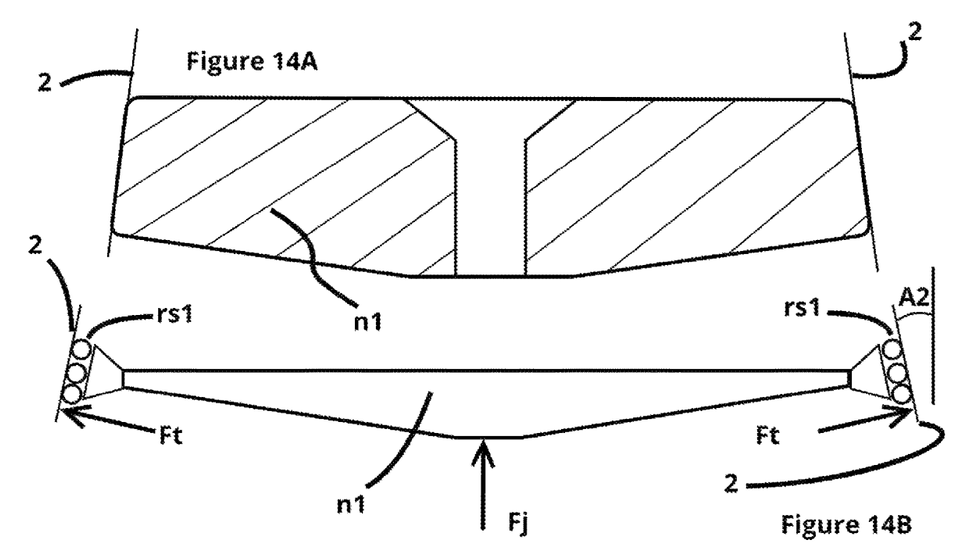

The present invention, nonetheless also benefits in that a second mechanism assists in amplification. With reference to FIG. 14A, the resilient element n1 is modelled as a rigid body, and the low friction between the resilient element wedge n1 and the restraining wall of coupling recess 2 against the self releasing machine taper angle A2 of the resilient element n1 per FIG. 14B is modelled substantially as a roller-sliding interface. In fact the use of a lubricant can be advantageously applied. The geometry of the situation is such that force Fj to generates reaction force Ft to equate at best to Ft=Fj/sin (A2), where Ft>>Fj. This again means an amplification of the force, where the amplification factor is between 1/sin A2>1 depending on the friction conditions, noting that if A2<30 degrees, then 1/sin A1>2 meaning that the amplification is greater than 2. Advantageously A2 as chosen to be nearer to 10°, meaning 1/sin A1=5.7, a maximum amplification factor of 5.7.

On account of both of these mechanisms, the axial force generated by a tightening the screwbolt/jacking fastener, is redirected and amplified by the wedge n1, subject to the wedge being such that upon deflection, the outer diameter increases—akin to the fashion in which a disk spring operates and that the wedge acts on a mating machine taper where the angle of the machine taper causes a radial reaction force that is always larger than the axial driving force on the wedge.

Figures 15A, 15B:
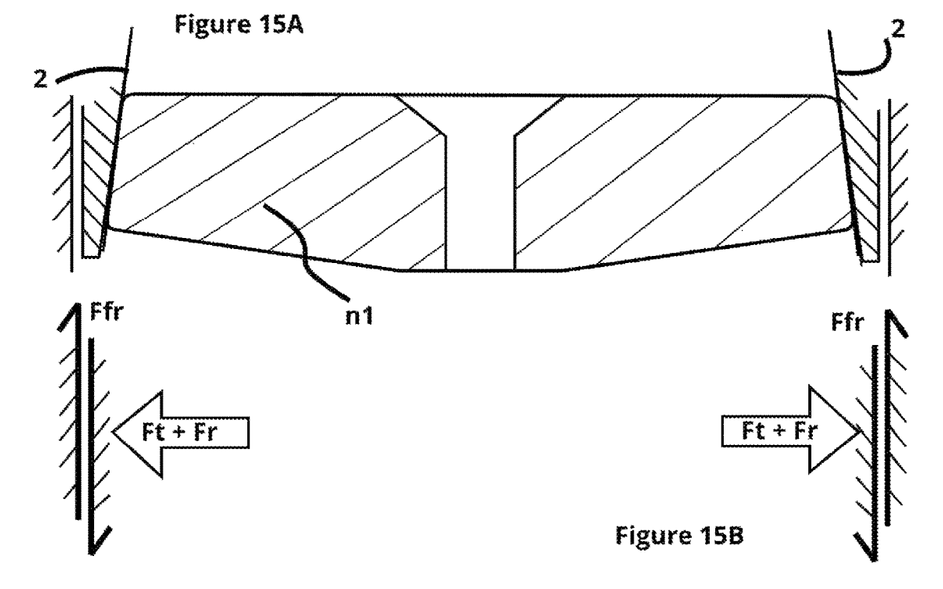

Due to the advantageous and ideal round circumferential shape of the resilient wedge contacting the mating adapter part, with reference to FIGS. 15A & B, a uniform force Ft+Fr is transferred through the clamped aspects of the adapter to create a friction force Ffr=(Ft+Fr)*C, where C is the friction coefficient between the contacting materials.

Figure 16A:
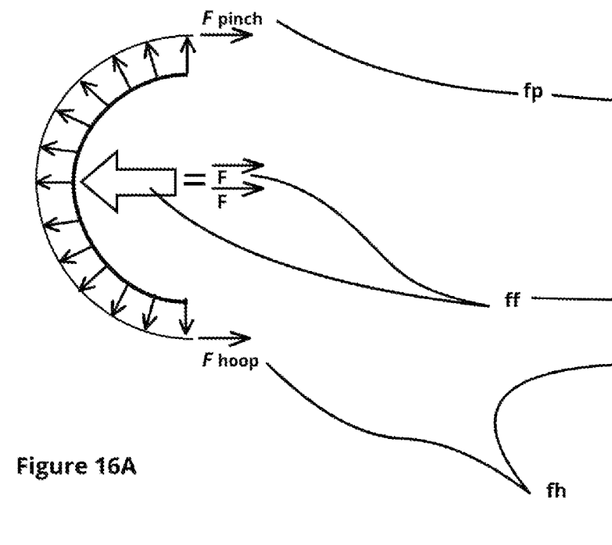
Figure 16B:
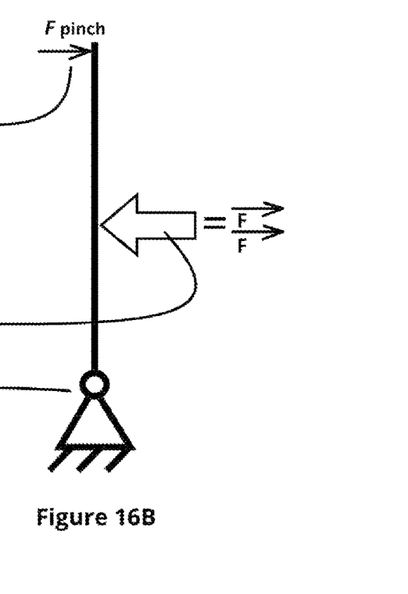

An analysis of a prior art clamping system with an external pinchbolt is effectively a lever arm system, where the pinching force Fpinch in FIGS. 16A & 16B is effectively hinged by balancing force Fhoop on the opposite side of the clamp. Depending on the friction coefficient between the clamp and restraining clamped-on mating part, an effective lever system is formed where at best the pinch force is amplified to a factor of 2 when the friction coefficient is zero, and the internal mating parts act in accordance with liquid and hoop stress phenomena. That is to say, the pinch and hoop forces add to a sum of forces Fpinch+Fhoop, such that, in lubricated conditions, will give an equally distributed load on the clamped part.

Figure 17A:
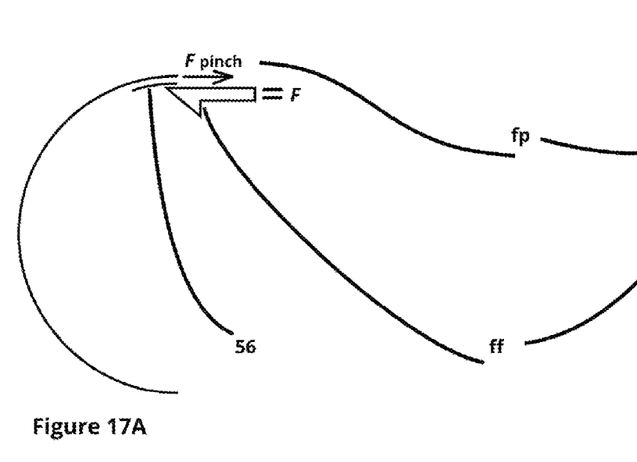
Figure 17B:
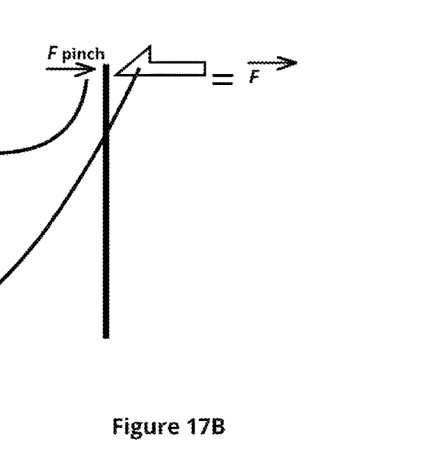

When the friction coefficient is 'infinite' (i.e. bonded), no slippage can occur between mating parts and the force equation is graphically displayed in FIGS. 17A & 17B, where the friction force ff opposes Fpinch (fp). This shows that the amplification of the clamping force theoretically achieves a maximum with a factor equal to 2 in a lubricated condition, and a minimum of 1 in a bonded condition. This means, in effect that in the case of severe friction all pinch forces Fpinch are balanced by a local reaction force F in the clamped part 56, meaning that the friction reduces the ability to transfer load evenly, needing more material in the clamped part to withstand material stress.

The invention claimed is:

1. A prosthesis including a first prosthetic limb component, a second prosthetic limb component, and a fastening system for fastening the first prosthetic limb component to the second prosthetic limb component,
    wherein the first prosthetic limb component is provided with a first coupling member and the second prosthetic limb component is provided with a second coupling member;
    wherein the first coupling member comprising a cylindric member having an axis, with a wall generally parallel with said axis;
    wherein the second coupling member comprises a circular skirt element having an axis and having corresponding external dimensions to the cylindric member whereby to permit a sliding fit therewith in an unfastened state;
    wherein the fastening system, associated with one of the first or second coupling members comprises a resilient member having an axis and wherein the resilient member is operable to expand laterally, orthogonally with respect to the axis, said axis being coaxial with the axis of the coupling member with which it is attached;
    wherein the fastening system is arranged such that, in a coupling mode of operation, the lateral expansion operates to cause the skirt to be in a state of frictional engagement with the other coupling member; and
    whereby the first and second coupling members couple together with associated first and second prosthetic limb components.

2. A prosthesis according to claim 1, wherein the first prosthetic limb component is a prosthetic limb and comprises one of a shin member, lower arm, foot or a hand, and the second prosthetic limb component is operable to receive a stump of a patient.

3. A prosthesis according to claim 1, wherein the first prosthetic limb component is a prosthetic limb and comprises one of a shin member, lower arm, foot or a hand, and the second prosthetic limb component comprises a coupling member having an additional coupling component and is operable to couple with a known coupling element associated with a prosthetic limb component that is operable to receive a stump of a patient.

4. A prosthesis according to claim 1, wherein the first prosthetic limb component is operable to receive a stump of a patient, and the second prosthetic limb component is a prosthetic limb and comprises one of a shin member, lower arm, foot or a hand.

5. A prosthesis according to claim 1, wherein the first prosthetic limb component comprises a coupling member having an additional coupling component operable to couple with a known coupling element associated with a prosthetic limb component that is operable to receive a stump of a patient and the second prosthetic limb component comprises a prosthetic limb being one of a shin member, lower arm, foot or a hand.

6. A prosthesis according to claim 1, wherein the cylindric member is a recess, and upon placement of the skirt within the recess and about the laterally expanding resilient member, the lateral expansion of the resilient member causes the exterior of the skirt to frictionally engage with inside walls of the recess.

7. A prosthesis according to claim 1, wherein the laterally expanding resilient member is selected from one of the following: a star nut; and an elastomeric material which can be compressed in a direction perpendicular to an axis of the cylindric member.

8. A prosthesis according to claim 1, wherein the inside wall surfaces of the skirt are tapered.

9. A prosthesis according to claim 1, wherein the resilient member is controlled by a cam-operated member or a screw-threaded member to expand laterally in a direction perpendicular to an axis of the cylindric member.

10. A prosthesis according to claim 1, wherein one or both of the cylindric and skirt members has a castellation.

11. A prosthesis according to claim 1, wherein the cylindric and skirt members have cooperating lips and grooves.

12. A prosthesis according to claim 1, wherein the cylindric and skirt members are generally circular in plan.

13. A prosthesis according to claim 1, wherein the cylindric and skirt members comprise corresponding polygons in plan.

* * * * *